United States Patent [19]
Strouth et al.

[11] 3,938,539
[45] Feb. 17, 1976

[54] APPARATUS FOR LEADING OFF AIR IN CONNECTION WITH THE MEASURING OF THE FLOW OF A LIQUID

[76] Inventors: Lennart Strouth, Bondegatan 5, 582 62 Linkoping; Claes Björkman, Grev Magnigatan 9 III, 114 55 Stockholm, both of Sweden

[22] Filed: June 14, 1974

[21] Appl. No.: 479,691

[30] Foreign Application Priority Data
June 15, 1973 Sweden ........................ 73084238

[52] U.S. Cl. ............... 137/202; 137/406; 137/558; 137/408; 137/433; 128/214 C
[51] Int. Cl.² ..................................... A61M 5/14
[58] Field of Search ...... 128/214 C, 214.2; 137/433, 137/174, 402, 209, 558, 559, 202, 408, 406

[56] References Cited
UNITED STATES PATENTS

| | | | |
|---|---|---|---|
| 2,416,267 | 2/1947 | Landon | 137/402 X |
| 2,844,147 | 7/1958 | Beacham | 137/433 X |

*Primary Examiner*—Alan Cohan
*Attorney, Agent, or Firm*—Browne, Beveridge, DeGrandi & Kline

[57] ABSTRACT

An apparatus for leading off air from liquid, preferably blood, and for measuring the flow of liquid through the apparatus which comprises two chambers separated by a partition formed with a throughflow aperture. One chamber is movable in relation to the other chamber and adapted, in relation to the amount of liquid in one or the other chamber, to control a valve regulating the build-up of pressure in the apparatus.

6 Claims, 3 Drawing Figures

APPARATUS FOR LEADING OFF AIR IN CONNECTION WITH THE MEASURING OF THE FLOW OF A LIQUID

This invention relates to an apparatus for leading off air in connection with the measuring of the flow of a liquid, for instance blood through an artificial kidney, said apparatus having an inlet chamber and an outlet chamber for the liquid, which chambers are separated from one another by a partition formed with a through-flow aperture for the liquid, the flow being measured by measurement of the liquid level in the inlet chamber.

In measuring, particularly of the flow of blood through an artifical kidney, apparatuses of this type have not functioned with satisfactory reliability to exclude that so-called air embolism arises during measurement. A fully controlled flow prevails when a patient is subjected to a dialysis treatment. Blood is sucked from the patient by means of a hose pump and the blood is pumped through a dialysis filter. The blood then passes a wholly closed bubble trap before it is sent back into the patient's body. If a leakage arises on the suction side of the pump air, instead of blood will be pumped under maintained pressure through the dialysis filter and via the bubble trap into the patient's body. In such a case the patient will immediately die from so-called air embolism, i.e. a clot containing air has entered the patient's blood stream. Such a leakage can arise for instance when the hose connection to the dialysis apparatus at the patient's body slips out of its fastening without anybody noticing it, as the patient may be sleeping.

The apparatus according to the present invention eliminates this serious drawback primarily in that there is provided between the outlet chamber and the ambient atmosphere a valve which from unactuated open position is adjustable into closed position by the liquid entering through the inlet chamber and thereby actuating the position of the inlet chamber. By this arrangement, the measuring device can be manufactured in a very simple and inexpensive manner, which is of particularly great importance when the device is used for measuring the flow of blood in a dialysis apparatus in which the measuring device is of the single-use type. The measuring device is also advantageous in that it provides, when used in a dialysis apparatus not only a measurement of the flow through the apparatus but also a separation of the bubbles in the liquid, the flow of which is measured, whereby the construction of the dialysis apparatus can be highly simplified.

Embodiments of the invention will be more fully described hereinbelow and with reference to the accompanying drawings in which FIG. 1 shows the measuring device when the outlet chamber is in communication with the atmosphere and no liquid flows through the measuring device;

Figure 1:
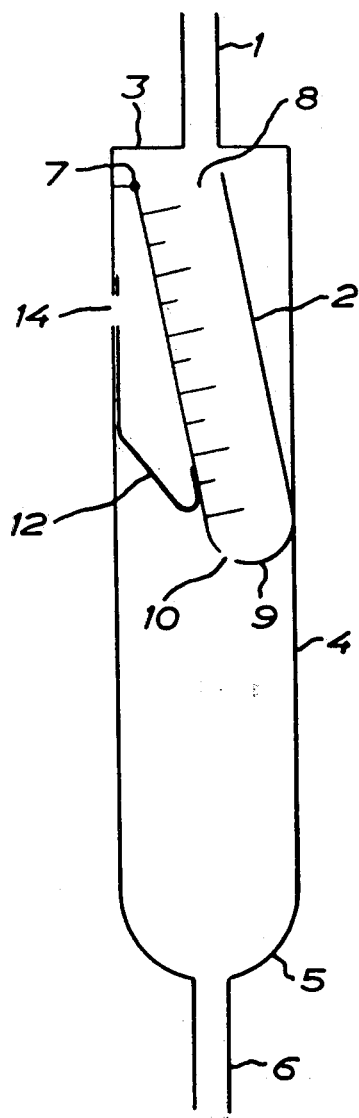
Figure 2:
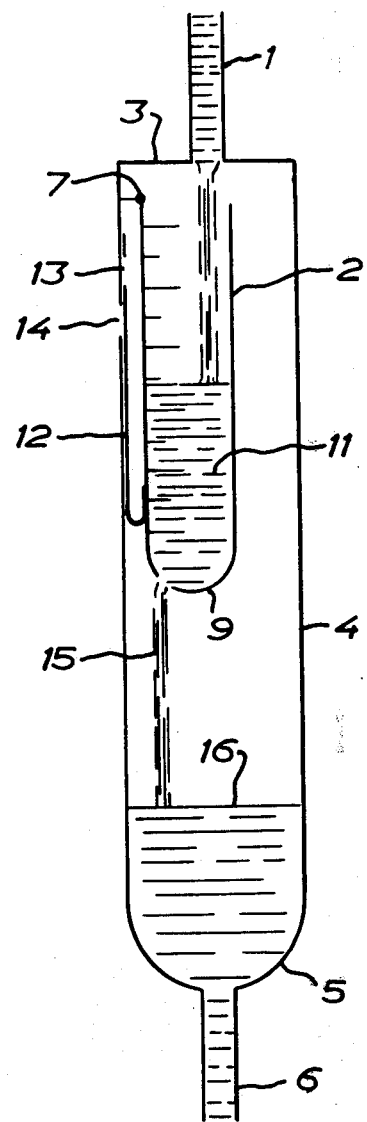
FIG. 2 shows the measuring device when the communication between the outlet chamber and the atmosphere is interrupted and a liquid flows through the measuring device.

The apparatus illustrated in FIGS. 1 and 2 is intended for leading off air and for measuring the flow of blood in an artificial kidney. Blood is sucked from the patient by means of a hose pump (not shown) and is pumped through a supply pipe 1 to an inlet chamber 2. The supply pipe 1 is inserted in an upper wall 3 of an outlet chamber 4 which is in the form of a tube and entirely encloses the inlet chamber 2. An outlet pipe 6 is inserted in the bottom 5 of the outlet chamber 4. Both the inlet chamber and the outlet chamber are made from transparent material.

The inlet chamber 2 is formed as a graduated measuring tube. A hinge 7 fixed to inner wall of the outlet chamber 4 in the uppermost portion thereof, supports the inlet chamber 2 so that it can pendulate from an outwardly swung position to a vertical position. The inlet chamber 2 has an open top part 8 which is positioned beneath and close to the point where the supply pipe 1 opens into the outlet chamber 4. The bottom 9 of the inlet chamber 2 is provided with an outlet aperture 10 for permitting the blood dammed up in the inlet chamber 2 to flow into the outlet chamber 4.

The movement of the inlet chamber 2 from its outwardly swung position to its vertical position takes place against the action of a spring 12 by the weight of the blood 11 dammed up in the inlet chamber 2. The spring 12 is a relatively thin leaf spring having a shape similar to an L. The upper half of the spring 12 is parallel with the side wall of the outlet chamber 4 and formed with a hole 13 which registers with a hole 14 in the side wall 4 when the spring 12 is shifted up and down in a guide provided on the inner side of the side wall of the outlet chamber 4. The lower half of the spring 12 is bent out towards the lower part of the inlet chamber 2 and fastened thereto.

When no blood flows through the measuring device the inlet chamber 2 occupies the outwardly swung position (the FIG. 1 position) by the action of the spring 12.

When the flow of blood commences the inlet chamber 2 is filled with blood 11 up to a level corresponding to the actual flow. By the weight of the blood 11 dammed up in the inlet chamber 2 a torque is produced about the hinge 7 so that the inlet chamber 2 will take the position illustrated in FIG. 2. As a result, the hole 13 movable with the spring 12 is moved past the hole 14 in the side wall of the outlet chamber 4 so that air cannot pass from the outlet chamber 4 into ambient atmosphere, but a pressure is built up in the measuring device. Under this pressure the blood 15 exiting from the inlet chamber 2 through the outlet aperture 10 to collect and form a blood level 16 in the lower part of the outlet chamber 4, is caused to flow through the outlet pipe 6 to the bubble trap and filter of the dialysis apparatus and from there flows back into the patient's body.

Should a leakage arise on the suction side of the pump, the hose pump will suddenly pump air and the flow of blood to the inlet chamber 2 ceases. The blood already contained in the inlet chamber 2 flows down into the outlet chamber 4. When the inlet chamber 2 has been emptied to a certain level, said chamber will take an oblique position by the action of the spring 12. When the spring 12 has been adjusted the holes 13 and 14 in the spring 12 and the outer chamber 4, respectively, will establish an open communication to the atmosphere outside the outlet chamber 4 so that the pressure will sink in the outlet chamber and in the entire circuit of the dialysis apparatus and the patient. The air pumped by the hose pump will freely exit into the atmosphere through the valve formed by the holes 13 and 14 and will not be forced into the patient's body. Since no pressure will build up, the blood level 16 in the outlet chamber 4 will be maintained almost unaltered and air cannot escape through the outlet pipe 6.

The holes 13 and 14 functioning as a valve will entirely prevent the risk that air is pumped into the patient's blood stream, which must be considered to be extremely valuable since the number of dialyses solely in Europe today amounts to about 1.8 millions and to an equal number in the USA and since risks of air embolism must be considered to exist in all of these dialyses.

Figure 3:
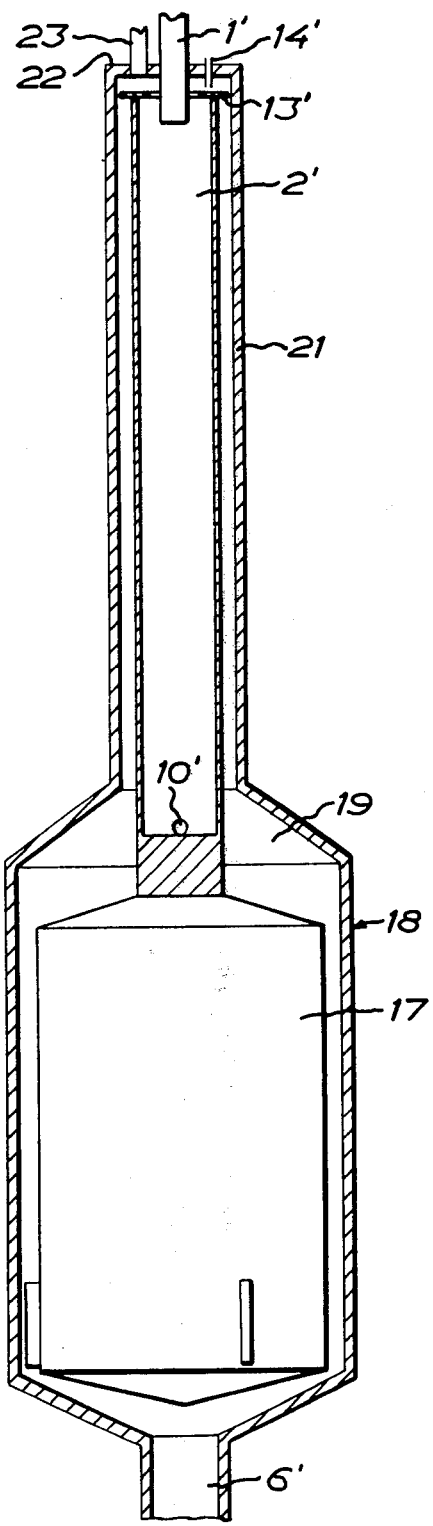
FIG. 3 shows a modified embodiment of the device.

The apparatus illustrated in FIG. 3 certainly differs in structural respect from the embodiment shown in FIGS. 1 and 2, but it functions in a similar way.

In FIG. 3 a supply pipe is designated 1'. The supply pipe opens at the upper open end of an inlet chamber 2' which preferably is graduated and is carried by a float 17 having guides. The float 17 and the inlet chamber 2' are contained in a housing 8 which is preferably made of a transparent material and provided at the bottom with an inlet 6'. The inlet chamber 2' at the bottom has an outlet aperture 10' which connects the interior of the chamber with the free space 19 in the housing 18 corresponding to the outlet chamber. The free space 19 surrounds the float 17 and the inlet chamber 2' and substantially has the same volume as said inlet chamber.

The upper end of the inlet chamber is provided with a transverse flange 13'. The upper portion 21 of the housing is formed as a neck and surrounds the inlet chamber. Said upper portion 21 is closed by means of a cover 22 through which extends the supply pipe 1'. Said cover also has a connecting socket 23 for a pressure gauge and a venting pipe 14'.

The venting pipe 14' extends some distance into the space beneath the cover and is intended for cooperation with the aforesaid transverse flange 13' of the inlet chamber, the inwardly facing end surface of the pipe 14' functioning as a valve seat against which the surface of the flange can be sealingly pressed.

The embodiment illustrated in FIG. 3 briefly functions as follows.

Blood enters the inlet chamber 2' through the supply pipe 1' and flows from said chamber into the space 19 in the housing 18. When the space 19 of the housing has been filled to the contemplated level the float 17 and thus the inlet chamber 2' are raised, the flange 13' of the inlet chamber closing the venting pipe 14 so that the contemplated build-up of pressure can take place.

Should an interruption of the blood supply occur through the supply pipe 1' the space 19 will be gradually emptied. As a result, the float 17 sinks and the venting pipe is opened so that no pressure build-up can take place.

What we claim and desire to secure by Letters Patent is:

1. For use in a closed-circuit pressurized conduit system through which blood is pumped from a patient through an artificial kidney or like treatment apparatus and returned to the patient, an apparatus for leading off air and preventing the build-up of air pressure in the system and for measuring the flow of blood through the system, said apparatus comprising an inlet chamber and an outlet chamber, inlet means adapted to be connected in the conduit system for directing the blood being pumped therethrough into said inlet chamber and outlet means adapted to be connected in the conduit system for directing blood from said outlet chamber into the conduit system, orifice means in the bottom portion of said inlet chamber providing a flow path from said inlet chamber into said outlet chamber, normally open vent means for venting said outlet chamber to atmosphere, said vent means including valve means operable between an open and a closed position, valve actuating means responsive to the level of blood in one of said chambers for moving said valve means to the closed position to permit build up of system pressure in said outlet chamber and to move said valve to the open position to vent said second chamber to atmosphere upon the blood level in said one chamber dropping below a predetermined level, and blood level measuring means carried by said inlet chamber indicating the level of blood above said orifice means and thereby providing a visible flow rate indication.

2. The apparatus as defined in claim 1 wherein said valve actuating means comprises said inlet chamber, said inlet chamber being mounted for movement within said outlet chamber in response to the level of blood in one of said chambers to move said valve between said open and said closed positions.

3. The apparatus as defined in claim 1 further comprising float means mounted in said outlet chamber and adapted to be floated by blood collected in said outlet chamber, said float means supporting said inlet chamber for movement therewith.

4. The apparatus as defined in claim 1 further comprising pivot means pendulously supporting said inlet chamber within said outlet chamber, resilient means urging said inlet chamber for movement about said pivot means from its normal at-rest position, said pivot means being located such that the weight of blood in said inlet chamber rotates said inlet chamber against the action of said resilient means to thereby move said valve from said open to said closed position.

5. The apparatus as defined in claim 4 wherein said resilient means comprises an elongated spring means having one end formed as a slide member of said valve means, the other end of said spring means engaging and being movable by said inlet chamber under the weight of blood collected therein.

6. The apparatus as defined in claim 5 wherein said spring means is a generally J-shaped leaf spring.

* * * * *